US009566217B2

(12) United States Patent
Tokunaga et al.

(10) Patent No.: US 9,566,217 B2
(45) Date of Patent: *Feb. 14, 2017

(54) HAIR CLEANSING COMPOSITION

(71) Applicant: KAO CORPORATION, Chuo-ku (JP)

(72) Inventors: Shinichi Tokunaga, Sumida-ku (JP); Tomoki Morioka, Utsunomiya (JP); Yuko Sugai, Kuku (JP)

(73) Assignee: KAO CORPORATION, Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/758,076

(22) PCT Filed: Dec. 12, 2013

(86) PCT No.: PCT/JP2013/083347
§ 371 (c)(1),
(2) Date: Jun. 26, 2015

(87) PCT Pub. No.: WO2014/103740
PCT Pub. Date: Jul. 3, 2014

(65) Prior Publication Data
US 2015/0352029 A1 Dec. 10, 2015

(30) Foreign Application Priority Data

Dec. 26, 2012 (JP) ................................. 2012-283747

(51) Int. Cl.
*A61K 8/02* (2006.01)
*A61K 8/46* (2006.01)
(Continued)

(52) U.S. Cl.
CPC .............. *A61K 8/0241* (2013.01); *A61K 8/46* (2013.01); *A61K 8/73* (2013.01); *A61K 8/84* (2013.01);
(Continued)

(58) Field of Classification Search
CPC ................. A61K 2800/412; A61K 2800/5426; A61K 8/0241; A61K 8/46; A61K 8/73; A61K 8/84; A61Q 5/00; A61Q 5/02; C11D 1/02; C11D 3/227; C11D 3/3723; C11D 3/3769
See application file for complete search history.

(56) References Cited

U.S. PATENT DOCUMENTS 4,371,517 A * 2/1983 Vanlerberghe ....... A61K 8/8147
424/70.11
5,183,601 A 2/1993 Jisai et al.
(Continued)

FOREIGN PATENT DOCUMENTS

JP 55-29563 A 3/1980
JP 4-41597 A 2/1992
(Continued)

OTHER PUBLICATIONS

International Search Report issued Mar. 11, 2014 in PCT/JP2013/083347 filed Dec. 12, 2013.
(Continued)

*Primary Examiner* — Aradhana Sasan
(74) *Attorney, Agent, or Firm* — Oblon, McClelland, Maier & Neustadt, L.L.P.

(57) ABSTRACT

A hair cleansing composition contains (a), (b), and (c). Component (a), as particles having mean particle size of 0.5-50 μm, is a polyalkyleneimine derivative or a salt thereof, having weight average molecular weight of 3,300-50,000, with at least one of $R^1$—CO—, $R^2$—$(CH_2)_n$—CHX—$CH_2$—, and $R^3$—NH—CO— bonded to 40 mol % or more of the N atoms of the polyalkyleneimine. In (a), $R^1$ represents H, alkyl, alkenyl, or the like; $R^2$ represents H, alkyl, alkoxy, alkenyl, or the like; n is 0 or 1; X represents H or OH; $R^3$ represents H, alkyl, or alkenyl; at least one of $R^1$ to $R^3$ has 13 or more carbon atoms, and the entirety of $R^1$ to $R^3$ has an average number of carbon atoms of 9 or more
(Continued)

and a linear group content of 30 mol % or more. Component (b) is an anionic surfactant. Component (c) is a water-soluble cationic polymer.

18 Claims, 1 Drawing Sheet

(51) Int. Cl.
 *A61K 8/73* (2006.01)
 *A61K 8/84* (2006.01)
 *A61Q 5/00* (2006.01)
 *A61Q 5/02* (2006.01)
 *C11D 3/22* (2006.01)
 *C11D 3/37* (2006.01)
 *C11D 1/02* (2006.01)

(52) U.S. Cl.
 CPC . *A61Q 5/00* (2013.01); *A61Q 5/02* (2013.01); *C11D 1/02* (2013.01); *C11D 3/227* (2013.01); *C11D 3/3723* (2013.01); *C11D 3/3769* (2013.01); *A61K 2800/412* (2013.01); *A61K 2800/5426* (2013.01)

(56) References Cited

U.S. PATENT DOCUMENTS

| | | |
|---|---|---|
| 5,409,628 A | 4/1995 | Heinz et al. |
| 5,576,279 A | 11/1996 | Pyles |
| 2002/0017627 A1 | 2/2002 | Fry et al. |
| 2002/0028910 A1 | 3/2002 | Fry et al. |
| 2003/0190335 A1 | 10/2003 | Boussouira et al. |
| 2009/0169502 A1 | 7/2009 | Quadir |
| 2014/0199253 A1 | 7/2014 | Hindley et al. |
| 2016/0000690 A1* | 1/2016 | Tokunaga ............ A61K 8/34 424/70.17 |

FOREIGN PATENT DOCUMENTS

| | | |
|---|---|---|
| JP | 4-74112 A | 3/1992 |
| JP | 05-194156 A | 8/1993 |
| JP | 6-172522 A | 6/1994 |
| JP | 6-299141 | 10/1994 |
| JP | 7-138136 | 5/1995 |
| JP | 7-188698 A | 7/1995 |
| JP | 09-157113 A | 6/1997 |
| JP | 2000-178145 A | 6/2000 |
| JP | 2003-286137 A | 10/2003 |
| JP | 2009-161762 | 7/2009 |
| JP | 2010-077061 A | 4/2010 |
| JP | 2012-140357 A | 7/2012 |
| JP | 2013-032326 A | 2/2013 |
| JP | 2013-216620 A | 10/2013 |
| JP | 2014-141485 A | 8/2014 |
| WO | 98/04233 | 2/1998 |
| WO | 2011/113680 A2 | 9/2011 |

OTHER PUBLICATIONS

International Preliminary Report on Patentability and Written Opinion issued Jul. 9, 2015 in PCT/JP2013/083347 filed Dec. 12, 2013 (submitting English translation only).
Extended European Search Report issued on Sep. 5, 2016 for European Patent Application No. 13868572.2.

* cited by examiner

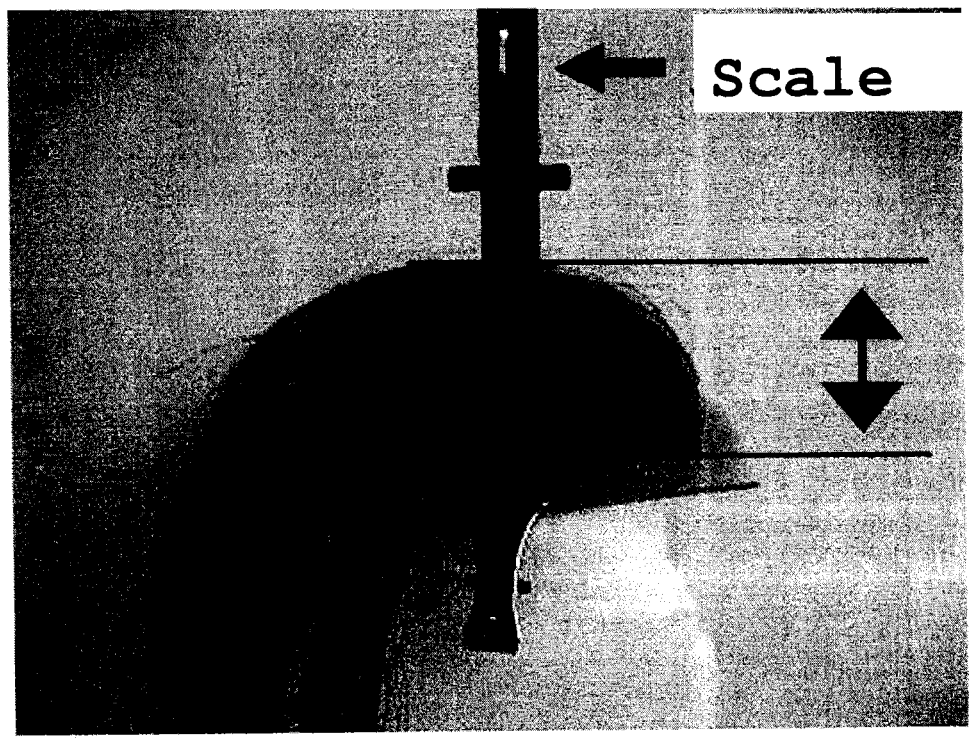

HAIR CLEANSING COMPOSITION

CROSS REFERENCE TO RELATED APPLICATION

This application is a 371 of PCT/JP2013/083347, filed on Dec. 12, 2013, and claims priority to Japanese Patent Application 2012-283747, filed on Dec. 26, 2012.

FIELD OF THE INVENTION

The present invention relates to a hair cleansing composition containing a high-molecular-weight polyalkyleneimine derivative or a salt thereof, the polyalkyleneimine derivative having substituents including a long-chain alkyl group or the like with high substitution degree.

BACKGROUND OF THE INVENTION

One of the common troubles in relation to the hair style is poor voluminous sensation of hair (hereinafter may be referred to as volume of hair). Complaints of such poor hair volume are generally heard from people who have thin hair or thin hair filaments. Thinning of hair or hair filaments aggravates with aging, and increases frequent use of a hair dye, which is generally applied to hair roots. Under such circumstances, people who are troubled with poor hair volume generally suffer from thinning of hair or hair filaments, as well as hair damage due to a chemical treatment; i.e., hydrophilization of the hair surface.

Poor hair volume is primarily caused by adhesion of hair to the scalp, which reduces rise of hair roots at the scalp. Such reduction of rise of hair roots is caused by hydrophilization of the hair surface due to a chemical treatment, as well as by thinning of hair or hair filaments, which reduces elasticity of hair. In other words, when the hair surface has been hydrophilized, difficulty is encountered in removal of water from hair tresses after towel drying, thereby increasing the time required for drying. In this case, people fail to have a stable hair style with a natural stream of healthy hair.

Hitherto, the volume of hair has been enhanced by, for example, semi-permanently modifying the hair style through permanent waving, or use of a styling product for keeping the hair style through modifying the interaction between hair fibers. In fact, these techniques increase the volume of hair. However, the former technique may cause hair damage, and the latter technique may provide unnatural hair sensation such as stickiness of hair or adhesion of hair filaments.

Meanwhile, a hair conditioning product such as a hair conditioner can increase the volume of hair by virtue of its base residing on hair surfaces. However, on a global basis, in some areas where many people having thin hair filaments desire to increase the hair volume, such a hair conditioner is not used very often. Therefore, it is considerably important to impart a function of increasing the volume of hair to a hair cleansing composition which can be routinely used.

Hitherto, some efforts have been made to impart a volume-increasing property to a hair cleansing composition. Patent Document 1 discloses a hair cleansing composition for increasing the hair volume containing a cationic polymer, a collagen derivative, and a polysiloxane in combination. Patent Document 2 discloses a hair wash containing elastic solid particles which can more effectively remain on the hair surface via coacervation. Besides techniques employing a hair cleansing composition, Patent Document 3 proposes a hair cosmetic composition which can promote drying of hair. The proposed cosmetic composition can enhance the speed of evaporation of water attached to hair by the mediation of co-boiling of lower alcohol and water, and can disentangle wet hair by means of spherical powder particles.

CITATION LIST

Patent Documents

Patent Document 1: JP-H05-194156 A
Patent Document 2: JP-2012-140357 A
Patent Document 3: JP-2003-286137 A

SUMMARY OF THE INVENTION

The present invention provides a hair cleansing composition which comprises the following components (a), (b), and (c), component (a) being in the form of particles having a mean particle size of from 0.5 µm to 50 µm, wherein the components (a), (b), and (c) are:

(a) a polyalkyleneimine derivative or a salt thereof, the derivative formed of a polyalkyleneimine having a weight average molecular weight of from 3,300 or more to 50,000 or less, in which at least one of the substituents represented by any of formulas (I), (II), and (III) is bonded to 40 mol % or more of the nitrogen atoms of the polyalkyleneimine, the formulas being:

$$R^1\text{---CO---} \quad (I)$$

$$R^2\text{---}(CH_2)_n\text{---}CHX\text{---}CH_2\text{---} \quad (II)$$

$$R^3\text{---}NH\text{---}CO\text{---} \quad (III)$$

[wherein, in formula (I), $R^1$ represents a group selected from the group consisting of a hydrogen atom, and an alkyl group, an alkenyl group, and a hydroxyalkyl group, in the form of a linear-chain group or a branched-chain group;

in formula (II), $R^2$ represents a group selected from the group consisting of a hydrogen atom, and an alkyl group, an alkoxy group, an alkenyl group, and an alkenyloxy group, in the form of a linear-chain group or a branched-chain group; n is an integer of 0 or 1; when $R^2$ is a hydrogen atom, a linear-chain or a branched-chain alkyl group, or a linear-chain or a branched-chain alkenyl group, n is 0; when $R^2$ is an alkoxy group or an alkenyloxy group, n is 1; and X represents a hydrogen atom or a hydroxyl group;

in formula (III), $R^3$ represents a group selected from the group consisting of a hydrogen atom, and an alkyl group and an alkenyl group, in the form of a linear-chain group or a branched-chain group; and $R^1$, $R^2$, and $R^3$ may be identical to or different from one another; the entirety of $R^1$, $R^2$, and $R^3$ has an average number of carbon atoms of 9 or greater; and the entirety of $R^1$, $R^2$, and $R^3$ has a linear group content of 30 mol % or more];

(b) an anionic surfactant; and
(c) a water-soluble cationic polymer.

The present invention also provides a method for increasing the volume of hair, the method comprising applying the aforementioned hair cleansing composition to hair, spreading the hair cleansing composition over the hair, and rinsing off the hair cleansing composition.

BRIEF DESCRIPTION OF THE DRAWINGS

FIG. 1 A photograph showing the method for evaluating ease of hair rising in the Examples.

DETAILED DESCRIPTION OF THE INVENTION

The technique disclosed in Patent Document 1 attains an insufficient volume-up effect due to stickiness provided by a liquid polysiloxane. The technique disclosed in Patent Document 2 attains an insufficient volume-up effect due to absence of a rapid drying property, since the hair wash cannot provide a hydrophobicizing effect to chemically damaged hair roots. The cosmetic composition of Patent Document 3 cannot include a desired amount of lower alcohol. Even if a certain amount of lower alcohol has been incorporated into the composition, the alcohol is removed through rinsing. In addition, the spherical powder particles can provide a rapid drying property only when they are co-present with the alcohol. Thus, application of the technique disclosed in Patent Document 3 to a hair cleansing composition is substantially impossible.

Thus, the present invention is to provide a hair wash which can impart a rapid-drying property to hair and increase the total volume of hair, even when the hair cleansing composition is applied to thin hair or thin hair filaments which have been frequently subjected to a chemical treatment.

As described above, rise of hair roots at the scalp is essential to realize voluminous hair sensation. For attaining rise of hair roots, the hair wash is required to provide a rapid hair drying property, so as not to complete hair set while the hair is adhered to the scalp. The present inventors found that such a rapid hair drying property can be attained by hydrophobicizing hair to thereby enhance dehydration and thin hair tresses after towel drying, and that the base of the hair wash is required to be firmly retained on the hair surface during rinsing of the hair, so as to hydrophobicize the hair.

The present inventors also found that the aforementioned performance can be attained by a hair cleansing composition produced by suspending a hydrophobic polyalkyleneimine derivative having a specific structure or a salt thereof in the co-presence of an anionic surfactant and a cationic polymer, to thereby control the particle size of the hydrophobic polyalkyleneimine derivative or a salt thereof to a specific value.

Component (a): Polyalkyleneimine Derivative or a Salt Thereof

Component (a) is a polyalkyleneimine derivative or a salt thereof, the derivative formed of a polyalkyleneimine having a weight average molecular weight of from 3,300 or more to 50,000 or less, in which at least one of the substituents represented by any of formulas (I), (II), and (III) is bonded to 40 mol % or more of the nitrogen atoms of the polyalkyleneimine, the formulas being:

$R^1$—CO— (I)

$R^2$—(CH$_2$)$_n$—CHX—CH$_2$— (II)

$R^3$—NH—CO— (III)

[wherein, in formula (I), $R^1$ represents a group selected from the group consisting of a hydrogen atom, and an alkyl group, an alkenyl group, and a hydroxyalkyl group, in the form of a linear-chain group or a branched-chain group;

in formula (II), $R^2$ represents a group selected from the group consisting of a hydrogen atom, and an alkyl group, an alkoxy group, an alkenyl group, and an alkenyloxy group, in the form of a linear-chain group or a branched-chain group; n is an integer of 0 or 1; when $R^2$ is a hydrogen atom, a linear-chain or a branched-chain alkyl group, or a linear-chain or a branched-chain alkenyl group, n is 0; when $R^2$ is an alkoxy group or an alkenyloxy group, n is 1; and X represents a hydrogen atom or a hydroxyl group;

in formula (III), $R^3$ represents a group selected from the group consisting of a hydrogen atom, and an alkyl group and an alkenyl group, in the form of a linear-chain group or a branched-chain group; and $R^1$, $R^2$, and $R^3$ may be identical to or different from one another, and at least one of $R^1$, $R^2$, and $R^3$ is a group having 13 or more carbon atoms; the entirety of $R^1$, $R^2$, and $R^3$ has an average number of carbon atoms of 9 or more; and the entirety of $R^1$, $R^2$, and $R^3$ has a linear group content of 30 mol % or more ].

The polyalkyleneimine, which is a source of component (a), is preferably a polyethyleneimine or a polypropyleneimine, with a polyethyleneimine having a branch structure being particularly preferred. The tertiary amino group content of the polyethyleneimine, based on the total amount of nitrogen atoms, is preferably about 10 mol % or more, more preferably 20 mol % or more, still more preferably 25 mol % or more, and preferably 40 mol % or less, more preferably 35 mol % or less. The weight average molecular weight (as determined through gel permeation chromatography (GPC) and reduced to pullulan) of the polyalkyleneimine is 3,300 or more, preferably 4,000 or more, more preferably 4,500 or more, still more preferably 5,000 or more, from the viewpoints of the effects of enhancing adsorption of component (a) on damaged portions of hair and facilitating provision of a conformation for realizing high alkyl group packing to thereby restore hydrophobicity and low hair friction in a wet state, imparting a rapid-drying property to hair to thereby prevent adhesion of hair to the scalp, and increasing the volume of hair. From the viewpoint of the effect of forming a stable gel-form composition, the molecular weight is 50,000 or less, preferably 40,000 or less, more preferably 30,000 or less, still more preferably 20,000 or less, yet more preferably 10,000 or less. Meanwhile, the weight average molecular weight of polyalkyleneimine determined through the method disclosed in the Examples of the present specification differs from a nominal molecular weight given by the manufacturer of the polyalkyleneimine. Specifically, the determined value is about from 1.5 to about 5 times the nominal value. Thus, in the present invention, the weight average molecular weight determined through the method disclosed in the Examples of the present specification is employed. Polyethyleneimine may be produced through a method generally known in the art, and such products are commercially available. Examples of commercial products of polyethyleneimine include EPOMIN (product of Nippon Shokubai, Co., Ltd.) and Lupasol (BASF).

The weight average molecular weight (as determined through gel permeation chromatography (GPC) and reduced to polystyrene) of the polyalkyleneimine derivative or a salt thereof—component (a)—is preferably 2,500 or more, more preferably 3,000 or more, still more preferably 3,500 or more, and preferably 50,000 or less, more preferably 40,000 or less, still more preferably 20,000 or less, yet more preferably 10,000 or less, from the viewpoints of the effects of enhancing adsorption of component (a) on damaged portions of hair and facilitating provision of a conformation for realizing high alkyl group packing to thereby restore hydrophobicity and low hair friction in a wet state, imparting a rapid-drying property to hair to thereby prevent adhesion of hair to the scalp, and increasing the volume of hair. The weight average molecular weight of the polyalkyleneimine derivative or a salt thereof—component (a)—employed in the present specification is also a value determined through the method disclosed in the Examples.

To polyalkyleneimine, the substituent represented by formula (I) may be added through a known method. In one procedure, a polyalkyleneimine is reacted with a fatty acid, a fatty acid ester, a fatty acid halide, or the like. When two or more species of the fatty acid, the fatty acid ester, the fatty acid halide, or the like are reacted, two or more substituents having different structures can be added. Such a synthesis method is disclosed in, for example, JP H09-157113 A.

To polyalkyleneimine, the substituent represented by formula (II) may be added through a known method. In one procedure, a polyalkyleneimine is reacted with an alkyl halide, an epoxyalkane, a glycidyl ether having an alkyl group or an alkenyl group, or the like. When two or more species of the alkyl halide, the epoxyalkane, the glycidyl ether having an alkyl group or an alkenyl group, or the like are reacted, two or more substituents having different structures can be added. Such a synthesis method is disclosed in, for example, JP H06-299141 A or JP 2009-161762 A.

To polyalkyleneimine, the substituent represented by formula (III) may be added through a known method. In one procedure, a polyalkyleneimine is reacted with an isocyanate having an alkyl group or an alkenyl group, or the like. When two or more species of the isocyanate having an alkyl group or an alkenyl group, or the like are reacted, two or more substituents having different structures can be added. Such a synthesis method is disclosed in, for example, JP S40-17661 B.

In the polyalkyleneimine derivative or a salt thereof (component (a)), the ratio of the amount of the substituent represented by formula (I), (II), or (III) to the total amount of the substituents represented by any of formulas (I), (II), and (III) is not limited. However, the ratio of the substituent represented by formula (I) is preferably from 20 mol % or more to 100 mol % or less, more preferably 40 mol % or more to 100 mol % or less, still more preferably 60 mol % or more to 100 mol % or less, yet more preferably from 80 mol % to 100 mol %. The ratio of the substituents represented by formulas (II) and (III) is preferably 0 mol % or more to 80 mol % or less, more preferably 0 mol % or more to 60 mol % or less, still more preferably 0 mol % or more to 40 mol % or less, yet more preferably 0 mol % or more to 20 mol % or less.

In the polyalkyleneimine derivative or a salt thereof (component (a)), the ratio of the number of nitrogen atoms of the polyalkyleneimine, which atoms are bonded to a substituent represented by any of formulas (I), (II), and (III), to the number of all nitrogen atoms; i.e., the substitution ratio, is 40 mol % or more among the nitrogen atoms of the polyalkyleneimine, preferably 45 mol % or more, more preferably 50 mol % or more, from the viewpoints of the effects of hydrophobicizing the hair surface, imparting a rapid-drying property to hair to thereby prevent adhesion of hair to the scalp, and increasing the volume of hair. The component (a) substitution ratio may be determined by, for example, calculating the ratio of the integrated area of the peak attributed to the polyalkyleneimine skeleton to that of the peak attributed to the relevant substituent, in measurement of an NMR spectrum of the produced polyalkyleneimine derivative or a salt thereof.

In formulas (I), (II), and (III), the alkyl group in $R^1$, $R^2$, or $R^3$ may be linear or branched. The number of carbon atoms of the alkyl group is preferably 1 or more, more preferably 2 or more, still more preferably 13 or more, yet more preferably 14 or more, and preferably 22 or less, more preferably 21 or less, still more preferably 18 or less, yet more preferably 17 or less, from the viewpoints of the effect of hydrophobicizing the hair surface, imparting a rapid-drying property to hair to thereby prevent adhesion of hair to the scalp, and increasing the volume of hair. The branch structure is preferably a methyl branch or an ethyl branch, with a methyl branch being more preferred. Specific examples of the alkyl group include myristyl, pentadecyl, cetyl, heptadecyl, stearyl, isostearyl, nonadecyl, eicosyl, behenyl, 14-methylhexadecyl, 16-methyloctadecyl, 18-methylnonadecyl, and 18-methyleicosyl.

In formulas (I), (II), and (III), the alkenyl group in $R^1$, $R^2$, or $R^3$ may have one or more unsaturated bonds, and may be linear or branched. From the viewpoints of the effects of hydrophobicizing the hair surface, imparting a rapid-drying property to hair to thereby prevent adhesion of hair to the scalp, and increasing the volume of hair, the number of carbon atoms of the alkenyl group is preferably 2 or more, more preferably 13 or more, still more preferably 14 or more, and preferably 22 or less, more preferably 21 or less, still more preferably 18 or less, yet more preferably 17 or less. From the viewpoint of the effect of reducing the friction of the hair surface, the branch structure is preferably a methyl branch or an ethyl branch, with a methyl branch being more preferred. Specific examples of the alkenyl group include tetradecenyl, pentadecenyl, hexadecenyl, heptadecenyl, octadecenyl, nonadecenyl, linolyl, linolenyl, and elaeostearyl.

In formula (I), the hydroxyalkyl group in $R^1$ may be linear or branched and preferably has one or two hydroxyl groups. The number of carbon atoms of the hydroxyalkyl group is preferably 1 or more, more preferably 2 or more, still more preferably 13 or more, yet more preferably 14 or more, and preferably 22 or less, more preferably 21 or less, still more preferably 18 or less, yet more preferably 17 or less. The branch structure is preferably a methyl branch or an ethyl branch, with a methyl branch being more preferred. Specific examples of the hydroxyalkyl group include 11-hydroxyheptadecyl, 8,9-bishydroxyheptadecyl, 3-hydroxyheptadecyl, 5-hydroxyeicosyl, and 12-hydroxystearyl.

In formula (II), the alkoxy group in $R^2$ may be linear or branched. From the viewpoints of the effects of enhancing hydrophobicity of the hair surface, imparting a rapid-drying property to hair to thereby prevent adhesion of hair to the scalp, and increasing the volume of hair, the number of carbon atoms of the alkenyl group is preferably 2 or more, more preferably 13 or more, and preferably 21 or less, more preferably 17 or less. From the viewpoint of the effect of reducing the friction of the hair surface, the branch structure is preferably a methyl branch or an ethyl branch, with a methyl branch being more preferred. Specific examples of the alkoxy group include myristyloxy, pentadecyloxy, cetyloxy, heptadecyloxy, stearyloxy, 16-methyloctadecyloxy, 18-methylnonadecyloxy, and 18-methyleicosyloxy.

In formula (II), the alkenyloxy group in $R^2$ may be linear or branched. From the viewpoints of the effects of enhancing hydrophobicity of the hair surface, imparting a rapid-drying property to hair to thereby prevent adhesion of hair to the scalp, and increasing the volume of hair, the number of carbon atoms of the alkenyl group is preferably 2 or more, more preferably 13 or more, and preferably 21 or less, more preferably 17 or less. From the viewpoint of the effect of reducing the friction of the hair surface, the branch structure is preferably a methyl branch or an ethyl branch, with a methyl branch being more preferred. Specific examples of the alkenyloxy group include tetradecenyloxy, pentadecenyloxy, hexadecenyloxy, heptadecenyloxy, octadecenyloxy, nonadecenyloxy, linolyloxy, linolenyloxy, and elaeostearyloxy.

$R^1$, $R^2$, and $R^3$ in formulas (I), (II), and (III) may be identical to or different from one another. A plurality of $R^1$s, a plurality of $R^2$s, and a plurality of $R^3$s may also be identical to or different from one another. From the viewpoints of the effects of restoring hydrophobicity of hair surface and low hair friction in a wet state, imparting a rapid-drying property to hair to thereby prevent adhesion of hair to the scalp, and increasing the volume of hair, the entirety of $R^1$, $R^2$, and $R^3$ preferably has an average number of carbon atoms of 9 or more, more preferably 12 or more. Among $R^1$, $R^2$, and $R^3$ in all the substituents, at least one group has a number of carbon atoms of 13 or more. The ≥13C group content is preferably 50 mol % or more, more preferably 70 mol % or more. From the viewpoints of the effects of restoring the hydrophobicity of the hair surface, imparting a rapid-drying property to hair to thereby prevent adhesion of hair to the scalp, and increasing the volume of hair, the entirety of $R^1$, $R^2$, and $R^3$ has a linear group content of 30 mol % or more, preferably 40 mol % or more. From the viewpoint of the effect of restoring low hair friction in a wet state, the linear group content is preferably 90 mol % or less, more preferably 80 mol % or less. From the viewpoint of the effect of restoring low hair friction in a wet state, the entirety of $R^1$, $R^2$, and $R^3$ preferably has a branched group content of 10 mol % or more, more preferably 20 mol % or more. From the viewpoints of the effects of restoring the hydrophobicity of the hair surface, imparting a rapid-drying property to hair to thereby prevent adhesion of hair to the scalp, and increasing the volume of hair, the branched group content is 70 mol % or less, preferably 60 mol % or less. From the viewpoints of restoring low hair friction in a wet state and the hydrophobicity of the hair surface, imparting a rapid-drying property to hair to thereby prevent adhesion of hair to the scalp, and increasing the volume of hair, $R^1$, $R^2$, and $R^3$ preferably have both a linear chain and a branched chain structure.

The polyalkyleneimine derivative of component (a) may be synthesized through addition of substituents represented by formulas (I), (II), and (III) individually. In one procedure, a substituent (I) is added to the polyalkyleneimine, to thereby yield an acylated polyalkyleneimine, and a substituent (II) is added to the acylated polyalkyleneimine. If needed, a substituent (III) is further added. Notably, the order of addition of the substituents (I), (II), and (III) may be determined as desired.

The polyalkyleneimine derivative of component (a) may be a salt form. Practically, a salt of the polyalkyleneimine derivative may also formed in the hair cosmetic composition of the present invention, by adding an acid for modifying the pH to the composition. Examples of the acid include acids having an alkyl group such as a fatty acid, an alkylphosphoric acid, an alkylsulfonic acid, and an alkylsulfuric acid; acidic amino acids such as L-glutamic acid and L-aspartic acid; pyroglutamic acid; aromatic acids such as benzoic acid and p-toluenesulfonic acid; hydroxy acids such as glycolic acid, lactic acid, glyceric acid, gluconic acid, pantothenic acid, malic acid, tartaric acid, and citric acid; other acids including phosphoric acid, hydrochloric acid, acetic acid, and succinic acid. Of these, from the viewpoint of the effect of moisturizing and softening hair, organic acids are preferred. Particularly, acidic amino acids, pyroglutamic acid, and hydroxy acids are preferred, with hydroxy acids being more preferred.

The polyalkyleneimine derivative or a salt thereof (component (a)) is preferably solid and water-insoluble at ambient temperature. The expression "component (a) is water-insoluble at ambient temperature" refers to the state in which component (a) added to pure water at 25° C. so as to have a concentration of at least 0.1% by mass or more is not dissolved to form a transparent solution, regardless of addition of an acid for neutralization (wherein the amount of the acid for neutralizing component (a) is not greater than the amount by equivalent of amino groups of component (a)). The expression "not dissolved to form a transparent solution" refers to the state in which a solution contains no solid such as aggregates or sediments which can be visually detected, and has a transmittance of 80% or more at 25° C. and 600 nm.

For restoring the hydrophobicity and low friction in a wet hair state, imparting a rapid-drying property to hair to thereby prevent adhesion of hair to the scalp, and increasing the volume of hair, component (a) preferably tends to spontaneously take a conformation for realizing high alkyl group packing.

Conventionally, the alkyl group packing property has been studied. Specifically, there has been measured the n-A isotherm of a polypropyleneimine dendrimer (Aihua Su et al., J. Phys. Chem. C 2007, 111, pp. 4695-4701) formed through incorporation of an alkyl group into an alkyl group-introduced PAMAM dendrimer (Tracy Zhang et al., Langmuir 2007, 23, pp. 10589-10597). It is reported that an amido group bonded to the foot of an alkyl group provides a hydrogen bond which enhances the alkyl group packing property.

The present inventors estimate that when the polyalkyleneimine derivative or a salt thereof has a specific molecular weight and alkyl group density, the alkyl group packing property can be enhanced. The inventors also assume that an excellent alkyl group packing property is a key to expression of hydrophobicity of hair surface and low friction in a wet state, imparting of a rapid-drying property to hair to thereby prevent adhesion of hair to the scalp, and an increase in hair volume.

The degree of alkyl group packing property may be assessed by measuring the π-A isotherm of the polyalkyleneimine derivative or a salt thereof, to thereby calculate the occupation area of one alkyl group.

Component (a) exhibits high alkyl group packing property. More specifically, according to the measured n-A isotherm, the occupation area of one alkyl group is small under low-pressure conditions, such as a surface pressure of 0.1 mN/m. In other words, according to the measured n-A isotherm of component (a), the occupation area of one alkyl group at a surface pressure of 0.1 mN/m is preferably 17 ($Å^2$) or less, more preferably 15 ($Å^2$) or less, still more preferably 13 ($Å^2$) or less.

From the viewpoints of adhesion of the hair cleansing composition onto the hair surface and persistency of the adhesion, the extent of needle penetration of component (a) of the hair cleansing composition of the present invention, as measured at 25° C. according to ASTM D1321, is preferably 2 or more, more preferably 4 or more, still more preferably 5 or more, yet more preferably 10 or more, further more preferably 15 or more, further more preferably 20 or more, and preferably 100 or less, more preferably 80 or less, still more preferably 70 or less.

From the viewpoint of sufficient expression of rapid drying property, component (a) of the hair cleansing composition of the present invention has a mean particle size of 0.5 μm or more, preferably 1 μm or more, still more preferably 2 μm or more. From the satisfactory stability of component (a) in the composition, the mean particle size is 50 μm or less, preferably 40 μm or less, still more preferably 30 μm or less, and the particles are suspended in the composition. As used herein, the mean particle size is a particle size determined by taking a photograph of particles of component (a) by means of an optical microscope under transmitted light, selecting at random 30 particles in the photograph, measuring the longest size in linear distance of each particle, and arithmetically averaging the distances.

When being incorporated into the hair cleansing composition of the present invention, component (a) of the present invention may be heated at a temperature equal to or higher than the melting point thereof, whereby the component is dispersed in the composition, and the particle size can be controlled to be a suitable size. In one mode of the procedure, a mixture of the anionic surfactant of component (b), the cationic polymer of component (c), and water is mixed with an optional solvent or an optional surfactant, and the resultant mixture is heated to a temperature equal to or higher than the melting point of component (a) (m.p. to m.p.+about 10° C.). To the thus-heated mixture, component (a) which has been heated to a temperature equal to or higher than the melting point of component (a) (m.p. to m.p.+about 10° C.) is added under stirring. Through tuning the type and amount of the surfactant, the type and amount of the cationic polymer, the viscosity of the mixture, the stirring rate, and other factors, the particle size of component (a) may be regulated. Notably, component (a) may be added directly to the composition as described above, or may be added as a suspension which has been prepared in advance.

Compounds of component (a) may be used singly or in combination of two or more species. From the viewpoints of the effects of hydrophobicizing the hair surface, imparting a rapid-drying property to hair to thereby prevent adhesion of hair to the scalp, and increasing the volume of hair, the component (a) content of the hair wash of the present invention is preferably 0.05% by mass or more, more preferably 0.1% by mass or more, still more preferably 0.15% by mass or more, yet more preferably 0.2% by mass or more, and preferably 10.0% by mass or less, still more preferably 3.0% by mass or less, yet more preferably 1.0% by mass or less, further more preferably 0.8% by mass or less.

[Component (b): Anionic Surfactant]

The anionic surfactant of component (b) is preferably a sulfuric acid-type surfactant, a sulfonic acid-type surfactant, and a carboxylic acid-type surfactant. Examples of the anionic surfactant include an alkylsulfate salt, a polyoxyalkylene alkyl ether sulfate salt, a polyoxyalkylene alkenyl ether sulfate salt, a sulfosuccinic acid alkyl ester salt, a sulfosuccinic acid alkylene alkyl phenyl ether sulfate salt, an alkanesulfonate salt, a higher fatty acid salt, and an alkyl ether carboxylic acid or a salt thereof. Of these, a polyoxyalkylene alkyl ether sulfate salt and an alkylsulfate salt are preferred, more preferably a surfactant represented by the following formula (IV) or (V):

RO(CH$_2$CH$_2$O)$_n$SO$_3$M  (IV)

ROSO$_3$M  (V)

[wherein R represents a C10 to C18 alkyl group or alkenyl group; M represents an alkali metal, an alkaline earth metal, or an ammonium; n is a weight-average number of from 1 to 5].

Among them, from the viewpoints of rapid lathering and favorable foam sensation, preferred is a polyoxyethylene alkyl ether sulfate salt represented by formula (IV), in which R is a C12 to C14 alkyl group, n is a weight average of 1, and M is an ammonium or sodium.

The anionic surfactants may be used singly or in combination of two or more species. From the viewpoints of the foamability and washing performance, the anionic surfactant content of the hair cleansing composition of the present invention is preferably 1% by mass or more, more preferably 5% by mass or more, still more preferably 8% by mass or more, yet more preferably 10% by mass or more. From the viewpoint of the pH of the hair cleansing composition in use thereof, the anionic surfactant content is preferably 30% by mass or less, more preferably 25% by mass or less, still more preferably 20% by mass or less.

Component (c): Water-sSoluble Cationic Polymer

The water-soluble cationic polymer of component (c) can enhance adhesion of component (a) to the hair surface via coacervation, whereby the hair volume can be increased.

Specific examples of the water-soluble cationic polymer include cationized cellulose, cationized starch, cationized guar gum, a diallyl quaternary ammonium salt-acrylamide copolymer, a vinylimidazolium trichloride-vinylpyrrolidone copolymer, a hydroxyethyl cellulose-dimethyldiallylammonium chloride copolymer, a vinylpyrrolidone-quaternarized dimethylaminoethyl methacrylate copolymer, a polyvinylpyrrolidone-alkylamino acrylate copolymer, a polyvinylpyrrolidone-alkylamino acrylate-vinylcaprolactam copolymer, a vinylpyrrolidone-methacrylamidopropyl (trimethylammonium) chloride copolymer, an alkylacrylamide-acrylate-alkylaminoalkylacrylamide-polyethylene glycol methacrylate copolymer, an adipic acid-dimethylaminohydroxypropylethylenetriamine copolymer (Cartaretine, product of Sandoz USA), and cationic polymers disclosed in JPH11-71435 A, JPS53-139734 A, and JPS60-36407 A. Of these, preferred are a cationized cellulose derivative, a cationized guar gum derivative, a diallyl quaternary ammonium salt-acrylamide copolymer, and an N,N-dimethylaminoethyl methacrylate diethylsulfate-N,N-dimethylacrylamide-polyethylene glycol dimethacrylate copolymer.

Examples of commercial products of the water-soluble cationic polymer which may be used in the invention include Merquat 550 (an acrylamide-diallyldimethylammonium salt copolymer, product of NALCO; INCI name: Polyquaternium-7), Lubiquat FC370 (a 1-vinyl-2-pyrrolidone-1-vinyl-3-methylimidazolium salt copolymer, product of BASF; INCI name: Polyquaternium-16), Gafquat 755N (a 1-vinyl-2-pyrrolidone-dimethylaminoethyl methacrylate copolymer, product of ISP; INCI name: Polyquaternium-11), Ucare polymer JR and LR series (a salt of a reaction product between trimethylammonium-substituted epoxide and hydroxyethyl cellulose, product of Amercol; INCI name: Polyquaternium-10), Poise C-60H, Poise C-80M, and Poise C-150L (a salt of a reaction product between trimethylammonium-substituted epoxide and hydroxyethyl cellulose, product of Kao Corporation; INCI name: Polyquaternium-10), Sofcare KG-301W and Sofcare KG-101W-E (an N,N-dimethylaminoethyl methacrylate diethylsulfate salt-N,N-dimethylacrylamide-polyethylene glycol dimethacrylate copolymer, product of Kao Corporation; INCI name: Polyquaternium-52), and Jaguar series (guar hydroxypropyltrimonium chloride, product of Rhodia).

The aforementioned water-soluble cationic polymers may be used singly or in combination of two or more species. From the viewpoint of the effect of increasing hair volume, the cationic polymer content of the hair cleansing composition of the present invention is preferably 0.01% by mass or more, more preferably 0.05% by mass or more, still more preferably 0.1% by mass or more, yet more preferably 0.2% by mass or more, further more preferably 0.3% by mass or more, further more preferably 0.4% by mass or more. So as not to inhibit foamability of the hair cleansing composition, the cationic polymer content is preferably 5% by mass or less, more preferably 2% by mass or less, still more preferably 1% by mass or less.

[Oily Agent and Solvent Having a Solubility Parameter δ of 20 or Less]

From the viewpoints of increasing the volume of hair, the hair cleansing composition of the present invention is preferably free from an oily agent or a solvent which has non-volatility and is liquid at ambient temperature in the amount that allows component (a) to be dissolved therein (the amount that causes an adverse effect due to dissolution of component (a)). The term "non-volatility" refers to a state in which the boiling point is 300° C. or higher at 25° C. and 1,013 hPa.

Such an oily agent or a solvent is one having a solubility parameter δ of 20 or less, except for a silicone, an oily agent or a solvent having a perfluoroalkyl group, and an amine. The solubility parameter δ (unit: $J^{1/2}$ $cm^{-3/2}$) refers to an estimated value calculated from the following equation.

$$\delta = (\Delta E_V / V_m)^{1/2} \quad \text{[Formula 1]}$$

$\Delta E_V$ [unit: kJmol$^{-1}$]: energy of vaporization per mole of liquid $V_m$ [unit: cm$^3$mol$^{-1}$]: molar volume $\Delta E_V = 2.54 \times 10^{-4} T_b^2$ $T_b$ [unit: K]: boiling point as measured In the case where the boiling point of the target compound has not been measured, $T_b$ may be calculated from the boiling point T[K] at a pressure p[mmHg] of measurement according to the following equation.

$$T_b = \{T^\alpha + (760^\alpha - p^\alpha)/A\}^{1/\alpha} \quad \text{[Formula 2]}$$

A=14.1
α=0.105

The boiling point $T_b$ of a sublimable or pyrolizable compound, which cannot be principally measured, may be estimated through a group contribution method by Hoy (Allan F. M. Barton, CRC Handbook of Solubility Parameters and Other Cohesion Parameters 2nd ed., CRC Press (1991), p. 165-167).

Specific examples of the oily agent or solvent having a solubility parameter δ of 20 or less include hydrocarbons such as squalane (δ=16.2), liquid paraffin (δ=16.4), and isopropyl palmitate (δ=17.2); and glycerides such as castor oil (δ=18.2), jojoba oil (δ=17.6), olive oil (δ=17.5), and high-oleic sunflower oil.

So long as an adverse effect due to dissolution of component (a) is avoided, the aforementioned oily agent or solvent which is liquid at ambient temperature and non-volatile may be incorporated into the hair cleansing composition of the present invention, for enhancing the stability of the composition. In the hair wash of the present invention, the ratio by mass of the total amount of the aforementioned oily agent and/or solvent to the amount component (a) is preferably 20 or less, more preferably 10 or less, still more preferably 5 or less, and preferably 0.01 or more, more preferably 0.1 or more. The total amount of the aforementioned oily agent and/or solvent with respect to the hair wash of the present invention is preferably 4.0% by mass or less, more preferably 2.0% by mass or less, still more preferably 1.5% by mass or less, and preferably 0.01% by mass or more, more preferably 0.1% by mass or more.

Nonionic surfactant

In order to enhance dispersion stability of component (a), the hair cleansing composition of the present invention may further contain a nonionic surfactant.

Examples of the nonionic surfactant include polyoxyalkylene sorbitan fatty acid ester, polyoxyalkylene sorbit fatty acid ester, polyoxyalkylene glycerin fatty acid ester, polyoxyalkylene fatty acid ester, polyoxyalkylene alkyl ether, polyoxyalkylene alkyl phenyl ether, polyoxyalkylene (hydrogenated) castor oil, sucrose fatty acid ester, polyglycerin alkyl ether, polyglycerin fatty acid ester, fatty acid alkanolamide, alkyl glycoside, alkyl glyceryl ether, and alkenyl glyceryl ether.

Among them, polyoxyalkylene alkyl ether, alkyl glyceryl ether, and alkenyl glyceryl ether are preferred. The polyoxyalkylene alkyl ether is preferably polyoxyethylene alkyl ether or polyoxypropylene alkyl ether. The polyoxyethylene alkyl ether is preferably a member represented by the following formula:

[wherein R' represents a C8 to C20 alkyl group or alkenyl group; and a is an average amount by mole of ethylene oxide of from 3 to 30].

R' is preferably a 010 to C18 alkyl group. The average amount by mole of ethylene oxide (a) is preferably from 10 to 20.

The polyoxyethylenealkyl ether preferably has an HLB (Griffin) of from 10 to 20, more preferably from 13 to 18. Specific examples include polyoxyethylene(16) lauryl ether (HLB 14.5; Emulgen 116, product of Kao Corporation), polyoxyethylene(10) cetyl ether (HLB 13.5; BC-10TX, product of Nikko Chemicals, Co., Ltd.), polyoxyethylene (15) cetyl ether (HLB 15.5; BC-15TX, product of Nikko Chemicals, Co., Ltd.), polyoxyethylene(20) stearyl ether (HLB 18; BS-20, product of Nikko Chemicals, Co., Ltd.), and polyoxyethylene(15) alkyl (sec-C12 to C14) ether (HLB 15.3; Softanol 150, product of Nippon Shokubai Co., Ltd.).

The polyoxypropylene alkyl ether is preferably a member represented by the following formula:

[wherein R" represents a C8 to C10 linear-chain or branched-chain alkyl group or alkenyl group; and b is a mass average number of 0.5 to 4].

Among them, from the viewpoints of rapid foaming and smooth rinsing, preferred is a polyoxypropylene octyl ether (wherein R" is a C8 alkyl group, and b is 2 to 3). A commercial product thereof is, for example, Sofcare GP-1 (product of Kao Corporation).

Examples of preferred nonionic surfactants include an alkyl glyceryl ether and an alkenyl glyceryl ether. Examples of preferred alkyl groups and alkenyl groups include C4 to C10 or C8 to C10, linear-chain or branched-chain alkyl groups. Specific examples include n-butyl, isobutyl, n-pentyl, 2-methylbutyl, isopentyl, n-hexyl, isohexyl, n-heptyl, n-octyl, 2-ethylhexyl, n-decyl, and isodecyl. Of these, 2-ethylhexyl and isodecyl are preferred.

Such nonionic surfactants may be used singly or in combination of two or more species. The nonionic surfactant content of the hair wash of the present invention is preferably 0.1% by mass or more, more preferably 0.5% by mass or more, and preferably 10% by mass or less, more preferably 8% by mass or less.

Other optional ingredients

Into the hair cleansing composition of the present invention, other ingredients generally employed in hair wash compositions may be incorporated in accordance with purposes. Examples of optional ingredients include amphoteric surfactants such as alkyldimethylaminoacetic acid betaine, fatty acid amidopropyl betaine, and alkyl hydroxysulfobetaine; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanate, and tridecyl isononanate; waxes such as beeswax, spermaceti, lanolin, and carnauba wax; alcohols such as ethanol, 1-propanol, 2-propanol, butanol, ethylene glycol, propylene glycol, benzyl alcohol, phenoxyethanol, 2-benzyloxyethanol, methyl carbitol, ethyl carbitol, propyl carbitol, butyl carbitol, triethylene glycol monoethyl ether, triethylene glycol monobutyl ether, and glycerin; silicones such as dimethyl polysiloxane and amino-modified silicone; anti-dandruff agents such as zinc pyrithione and benzalkonium chloride; vitamins; antibacterials; anti-inflammatory agents; antiseptics; chelating agents; humectants such as panthenol; colorants such as a dye and a pigment; extracts such as *Eucalyptus Globulus* polar solvent extract, a protein or a hydrolyzate thereof obtained from shells having a nacreous layer or pearl, a protein or a hydrolyzate thereof obtained from silk, a protein-containing extract obtained from seeds of leguminous plant, Panax ginseng extract, rice germ extract, *Fucus* extract, *Camellia* extract, *Aloe* extract, *Alpinia* zerumbet leaf extract, and *Chlorella Vulgaris* extract; pearl powder products such as titanated mica; perfumes; dyes; UV-absorbers; antioxidants; and other ingredients disclosed in ENCYCLOPEDIA OF SHAMPOO INGREDIENTS (MICELLE PRESS).

These ingredients include the aforementioned oily agent or solvent which is liquid at ambient temperature and has non-volatility; i.e., an oily agent and a solvent having a solubility parameter δ of 20 or less. However, as described above, such ingredients may be used, so long as an adverse effect due to dissolution of component (a) is avoided.

The hair cleansing composition of the present invention preferably contains at least water as a medium. That is, the composition of the invention is preferably an aqueous hair cleansing composition.

pH

From the viewpoint of enhancing the stability of the hair wash of the present invention, the pH of the hair cleansing composition is preferably 2.0 or more, more preferably 2.5 or more, still more preferably 3.0 or more, yet more preferably 3.5 or more, further more preferably 4.0 or more. From the viewpoint of enhancing adsorption of component (a) onto hair, the pH is preferably 7.5 or less, more preferably 6.5 or less, still more preferably 5.5 or less. Notably, in the present invention, the pH of the hair cleansing composition is defined as a pH value of a 20-fold by mass water dilution of the composition determined at 25° C.

Method for Increasing Hair Volume

For increasing the volume of hair by use of the hair cleansing composition of the present invention, a technique similar to a hair cleansing method by use of a conventional hair cleansing composition may be employed. That is, the hair wash of the present invention is applied onto hair, the applied hair cleansing composition is spread over the hair, and then the hair cleansing composition is rinsed off, to thereby increase the volume of the hair.

In addition to the aforementioned embodiments of the invention, further preferred embodiments will next be described.

<1>

A hair cleansing composition which comprises the following components (a), (b), and (c), component (a) being in the form of particles having a mean particle size of from 0.5 μm or more to 50 μm or less, wherein the components (a), (b), and (c) are:

(a) a polyalkyleneimine derivative or a salt thereof, the derivative formed of a polyalkyleneimine having a weight average molecular weight of from 3,300 or more to 50,000 or less, in which at least one of the substituents represented by any of formulas (I), (II), and (III) is bonded to 40 mol % or more of the nitrogen atoms of the polyalkyleneimine, the formulas being:

$$R^1—CO—  \quad (I)$$

$$R^2—(CH_2)_n—CHX—CH_2— \quad (II)$$

$$R^3—NH—CO— \quad (III)$$

[wherein, in formula (I), $R^1$ represents a group selected from the group consisting of a hydrogen atom, and an alkyl group, an alkenyl group, and a hydroxyalkyl group, in the form of a linear-chain group or a branched-chain group;

in formula (II), $R^2$ represents a group selected from the group consisting of a hydrogen atom, and an alkyl group, an alkoxy group, an alkenyl group, and an alkenyloxy group, in the form of a linear-chain group or a branched-chain group; n is an integer of 0 or 1; when $R^2$ is a hydrogen atom, a linear-chain or a branched-chain alkyl group, or a linear-chain or a branched-chain alkenyl group, n is 0; when $R^2$ is an alkoxy group or an alkenyloxy group, n is 1; and X represents a hydrogen atom or a hydroxyl group;

in formula (III), $R^3$ represents a group selected from the group consisting of a hydrogen atom, and an alkyl group and an alkenyl group, in the form of a linear-chain group or a branched-chain group; and $R^1$, $R^2$, and $R^3$ may be identical to or different from one another, and at least one of $R^1$, $R^2$, and $R^3$ is a group having 13 or more carbon atoms; the entirety of $R^1$, $R^2$, and $R^3$ has an average number of carbon atoms of 9 or more; and the entirety of $R^1$, $R^2$, and $R^3$ has a linear group content of 30 mol % or more];

(b) an anionic surfactant; and (c) a water-soluble cationic polymer.

<2>

The hair cleansing composition as described in <1>, wherein, in component (a), the ratio of the number of nitrogen atoms, which atoms are bonded to a substituent represented by any of formulas (I), (II), and (III), to the number of all nitrogen atoms of the polyalkyleneimine is preferably 45 mol % or more, more preferably 50 mol % or more.

<3>

The hair cleansing composition as described in <1> or <2>, wherein, in component (a), the ratio of the number of groups represented by formula (I) to the number of all substituents is preferably 20 mol % or more, more preferably 40 mol % or more, still more preferably 60 mol % or more, yet more preferably 80 mol % or more, and the ratio of the total number of groups represented by formulas (II) and (III) to the number of all substituents is preferably 80 mol % or less, more preferably 60 mol % or less, still more preferably 40 mol % or less, yet more preferably 20 mol % or less.

<4>

The hair cleansing composition as described in any of <1> to <3>, wherein, in component (a), the entirety of $R^1$, $R^2$, and R³ preferably has a linear group content of 40 mol % or more, and 90 mol % or less, more preferably 80 mol % or less.

<5>

The hair cleansing composition as described in any of <1> to <3>, wherein, in component (a), the entirety of R¹, R², and R³ preferably has a branched group content of 10 mol % or more, more preferably 20 mol % or more, and 60 mol % or less.

<6>

The hair cleansing composition as described in <4>, wherein, in component (a), the entirety of R¹, R², and R³ preferably has a linear group content of 30 mol % or more to 90 mol % or less and a branched group content of 10 mol % or more to 70 mol % or less.

<7>

The hair cleansing composition as described in <4>, wherein, in component (a), the entirety of R¹, R², and R³ preferably has a linear group content of 40 mol % or more to 80 mol % or less and a branched group content of 20 mol % or more to 60 mol % or less.

<8>

The hair cleansing composition as described in any of <1> to <7>, wherein, in component (a), the entirety of R¹, R², and R³ preferably has an average number of carbon atoms of 12 or more.

<9>

The hair cleansing composition as described in any of <1> to <8>, wherein the polyalkyleneimine, which is a source of component (a), preferably has a weight average molecular weight of 4,000 or more, more preferably 4,500 or more, still more preferably 5,000 or more, and preferably 40,000 or less, more preferably 30,000 or less, still more preferably 20,000 or less, yet more preferably 10,000 or less.

<10>

The hair cleansing composition as described in any of <1> to <9>, wherein the polyethyleneimine, which is a source of component (a), preferably has a tertiary amino group content of the polyethyleneimine, based on the total amount of nitrogen atoms, of 10 mol % or more, more preferably 20 mol % or more, still more preferably 25 mol % or more, and preferably 40 mol % or less, more preferably 35 mol % or less.

<11>

The hair cleansing composition as described in any of <1> to <10>, wherein the polyalkyleneimine derivative or a salt thereof, which is component (a), preferably has a weight average molecular weight of 2,500 or more, more preferably 3,000 or more, still more preferably 3,500 or more, and preferably 50,000 or less, more preferably 40,000 or less, still more preferably 20,000 or less, yet more preferably 10,000 or less.

<12>

The hair cleansing composition as described in any of <1> to <11>, which has an extent of needle penetration of component (a), as measured at 25° C. according to ASTM D1321, of preferably 2 or more, more preferably 4 or more, still more preferably 5 or more, yet more preferably 10 or more, further more preferably 15 or more, further more preferably 20 or more, and preferably 100 or less, more preferably 80 or less, still more preferably 70 or less.

<13>

The hair cleansing composition as described in any of <1> to <12>, wherein the component (a) content is preferably 0.05% by mass or more, more preferably 0.1% by mass or more, still more preferably 0.15% by or more, yet more preferably 0.2% by mass or more, and preferably 10.0% by mass or less, more preferably 3.0% by mass or less, still more preferably 1.0% by or less, yet more preferably 0.8% by mass or less.

<14>

The hair cleansing composition as described in any of <1> to <13>, wherein the anionic surfactant of component (b) is preferably a member selected from the group consisting of a sulfuric acid-type surfactant, a sulfonic acid-type surfactant, and a carboxylic acid-type surfactant.

<15>

The hair cleansing composition as described in any of <1> to <13>, wherein the anionic surfactant of component (b) is preferably a member selected from the group consisting of an alkylsulfate salt, a polyoxyalkylene alkyl ether sulfate salt, a polyoxyalkylene alkenyl ether sulfate salt, a sulfosuccinic acid alkyl ester salt, a sulfosuccinic acid alkylene alkyl phenyl ether sulfate salt, an alkanesulfonate salt, a higher fatty acid salt, and an alkyl ether carboxylic acid or a salt thereof.

<16>

The hair cleansing composition as described in any of <1> to <13>, wherein the anionic surfactant of component (b) is a surfactant represented by the following formula (IV) or (V):

$$RO(CH_2CH_2O)_nSO_3M \qquad (IV)$$

$$ROSO_3M \qquad (V)$$

[wherein R represents a C10 to C18 alkyl group or alkenyl group; M represents an alkali metal, an alkaline earth metal, or an ammonium; n is a weight-average number of from 1 to 5].

<17>

The hair cleansing composition as described in any of <1> to <16>, wherein the component (b) content is preferably 1% by mass or more, more preferably 5% by mass or more, still more preferably 8% by mass or more, yet more preferably 10% by mass or more, and preferably 30% by mass or less, more preferably 25% by mass or less, still more preferably 20% by or less.

<18>

The hair cleansing composition as described in any of <1> to <17>, wherein the water-soluble cationic polymer of component (c) is preferably a member selected from the group consisting of a cationized cellulose derivative, a cationized guar gum derivative, a diallyl quaternary ammonium salt-acrylamide copolymer, and an N,N-dimethylaminoethyl methacrylate diethylsulfate-N,N-dimethylacrylamide-polyethylene glycol dimethacrylate copolymer.

<19>

The hair cleansing composition as described in any of <1> to <18>, wherein the component (c) content is preferably 0.01% by mass or more, more preferably 0.05% by mass or more, still more preferably 0.1% by mass or more, yet more preferably 0.2% by mass or more, further more preferably 0.3% by mass or more, further more preferably 0.4% by mass or more, and preferably 5% by mass or less, more preferably 2% by mass or less, still more preferably 1% by mass or less.

<20>

The hair cleansing composition as described in any of <1> to <19>, wherein the ratio of the total amount of the non-volatile solvent and oily agent which are liquid at ambient temperature and have a solubility parameter δ of 20 or less to the amount of component (a) is preferably 20 or less, more preferably 10 or less, still more preferably 5 or less, and preferably 0.01 or more, more preferably 0.1 or more.

<21>

The hair cleansing composition as described in any of <1> to <20>, wherein the total amount of the non-volatile solvent and oily agent which are liquid at ambient temperature and have a solubility parameter S of 20 or less is preferably 4.0% by mass, more preferably 2.0% by mass or less, still more preferably 1.5% by mass or less, and preferably 0.01% by mass or more, more preferably 0.1% by bass or more.

<22>

The hair cleansing composition as described in any of <1> to <21>, which preferably contains at least water as a medium.

<23>

A method for increasing the volume of hair, comprising applying to hair a hair wash as recited in any of <1> to <22>, spreading the hair cleansing composition over the hair, and rinsing off the hair cleansing composition.

<24>

Use of a hair cleansing composition for increasing the volume of hair by applying to hair a hair cleansing composition as recited in any of <1> to <22>, spreading the hair cleansing composition over the hair, and rinsing off the hair cleansing composition.

EXAMPLES

Production Example 1

Polyalkyleneimine Derivative (1)

Polyethyleneimine (EPOMIN SP018, molecular weight: 1,800 (manufacturer's nominal value), product of Nippon Shokubai, Co., Ltd.) (40 g) was heated, and stearic acid (Lunac S-98; product of Kao Corporation) (140 g) was added thereto. Under a stream of nitrogen, the mixture was heated to 180° C. and stirred for 18 hours, to thereby yield polyethyleneimine derivative (1) in which 50 mol % of the nitrogen atoms of polyethyleneimine were acylated.

Production Example 2

Polyalkyleneimine Derivative (2)

The procedure of Production Example 1 was repeated, except that polyethyleneimine (Lupasol PR8515, molecular weight: 2,000 (manufacturer's nominal value), product of BASF) (40 g), stearic acid (Lunac S-98, product of Kao Corporation) (86.8 g), isostearic acid (52.1 g) (Isostearic acid EX, product of Kokyu Alcohol Kogyo Co., Ltd.), and acetic acid (11.7 g) were used, to thereby yield polyethyleneimine derivative (2) in which 70% of the nitrogen atoms of polyethyleneimine were acylated. The derivative (2) was found to have a ratio by mole of linear-chain alkyl to branched-chain alkyl of 73: 27.

Production Examples 3 to 11

Polyalkyleneimine Derivatives (3) to (11)

The procedures of Production Examples 1 and 2 were repeated, whereby reaction between polyalkyleneimine and fatty acid was performed, to thereby yield polyalkyleneimine derivatives (3) to (11).

Production Example 12

Polyalkyleneimine Derivative (12)

Polyethyleneimine (EPOMIN SP012, molecular weight: 1,200 (manufacturer's nominal value), weight average molecular weight (as measured): 4,250, product of Nippon Shokubai, Co., Ltd.) (40 g) was heated, and isostearyl glycidyl ether (disclosed in JPS56-142275 A) (27 g) was added thereto. Under a stream of nitrogen, the mixture was heated to 80° C. and allowed to react for 4 hours. Subsequently, stearic acid (Lunac S-98, product of Kao Corporation) (100 g) was added to the reaction mixture. The resultant mixture was heated to 180° C. and allowed to react for 8 hours, to thereby yield polyethyleneimine derivative (12). In the derivative (12), about 9 mol % of the nitrogen atoms of polyethyleneimine were alkylated (i.e., bonded to a substituent represented by formula (II)) and about 36 mol % of the nitrogen atoms were acylated (i.e., bonded to a substituent represented by formula (I)).

Production Example 13

Polyalkyleneimine Derivative (13)

Polyethyleneimine (Lupasol G20 waterfree, molecular weight: 1,300 (manufacturer's nominal value), weight average molecular weight (as measured): 3,500, product of BASF (40 g) was dissolved in toluene (100 g), and the solution was heated to 100° C. under a stream of nitrogen. Octadecyl isocyanate (product of Wako Pure Chemical Industries, Ltd.) (49.4 g) was added dropwise to the heated solution, and the mixture was allowed to react for 4 hours. Subsequently, stearic acid (Lunac S-98, product of Kao Corporation) (42.2 g) and isostearic acid (Isostearic acid EX, product of Kokyu Alcohol Kogyo Co., Ltd.) (26.4 g) were added to the reaction mixture. While toluene was removed through distillation, the resultant mixture was heated to 180° C. and allowed to react for 8 hours, to thereby yield polyethyleneimine derivative (13). In the derivative (13), about 20 mol % of the nitrogen atoms of polyethyleneimine were ureated (i.e., bonded to a substituent represented by formula (III)) and about 30 mol % of the nitrogen atoms were acylated (i.e., bonded to a substituent represented by formula (I)).

Production Example 14

Polyalkyleneimine Derivative (14)

Polyethyleneimine (EPOMIN SP012, molecular weight: 1,200 (manufacturer's nominal value), weight average molecular weight (as measured): 4,250, product of Nippon Shokubai, Co., Ltd.) (40 g) was heated, and stearyl glycidyl ether (72 g) and isostearyl glycidyl ether (disclosed in JPS56-142275 A) (48 g) were added thereto. Under a stream of nitrogen, the mixture was heated to 80° C. and allowed to react for 8 hours, to thereby yield polyethyleneimine derivative (14). In the derivative (14), about 40 mol % of the nitrogen atoms of polyethyleneimine were alkylated (i.e., bonded to a substituent represented by formula (II)).

Table 1 shows data of polyalkyleneimine derivatives produced in Production Examples 1 to 14. The data include the molecular weights (manufacturer's nominal values, and measured weight average molecular weights) of polyethyleneimines serving as raw materials, the weight average molecular weights (as measured) of formed polyalkyleneimine derivatives, the nitrogen atom substitution ratios (mol%), the numbers of carbon atoms in $R^1$, $R^2$, and $R^3$, the average numbers of alkyl carbon atoms in the substituents, the C≥13 contents of the alkyl groups, and the linear/branch balances of the alkyl groups, the specific substituent ratios, and the extent of needle penetration (by ASTM D1321).

The weight average molecular weights of the polyalkyleneimines and polyalkyleneimine derivatives or a salt thereof, and the extents of needle penetration of polyalkyleneimine derivatives or a salt thereof were determined under the following conditions.

<Weight Average Molecular Weight Measurement Conditions>

Conditions 1 (Measurement Conditions for Polyalkyleneimines Serving as Raw Materials of Component (a))

Each polyalkyleneimine was dissolved in eluent 1, to thereby form a 0.1% by mass solution, and the solution was analyzed through GPC under the following conditions, whereby weight average molecular weights as reduced to pullulan were determined.

GPC Measurement Conditions

Column: two columns of TSK gel α-M (product of Tosoh Corporation)

Eluent 1: 0.15-mol/L sodium sulfate, 1% by mass acetic acid/water

Flow rate: 1.0 mL/min, Column temperature: 40° C.

Detector: refractive index detector

Conditions 2 (Measurement Conditions for Component (a))

Each polyalkyleneimine derivative was dissolved in eluent 2, to thereby form a 0.5% by mass solution, and the solution was analyzed through GPC under the following conditions, whereby weight average molecular weights as reduced to polystyrene were determined.

GPC Measurement Conditions

Column: two columns of K-804L (product of Shodex)

Eluent 2: 0.1 mol/L N,N-dimethyldodecylamine (Farm=DM2098 (product of Kao Corporation))/chloroform Flow rate: 1.0 mL/min, Column temperature: 40° C.

Detector: refractive index detector

<Measurement of Extent of Needle Penetration>

Each component (a) was melted by heat and then cooled to thereby prepare a sample, and the extent of needle penetration of the sample was measured at 25° C. by means of a Testing Apparatus for Penetration (product of Nikka Engineering).

Specifically, the sample was melted at about 70° C., and the molten sample was poured into a container (inner diameter: about 20 mm, height: about 20 mm, and wall thickness: about 1 mm). The sample was allowed to cool at room temperature (22 to 26° C.) for one hour. A predetermined needle having a total mass of 100 g was orthogonally penetrated into the sample for 5 seconds. The needle penetration depth was determined by means of a dial gauge. The extent of needle penetration of the sample was determined by measuring the needle penetration depth to the order of 0.1 mm, and multiplying the value by 10. The measurement was conducted thrice, and the values were averaged. The averaged value was rounded off to the zero decimal place, to thereby obtain the extent of needle penetration.

TABLE 1

| | | Polyalkyleneimine derivative | | | | | | | | | | | | | |
|---|---|---|---|---|---|---|---|---|---|---|---|---|---|---|---|
| | | (1) | (2) | (3) | (4) | (5) | (6) | (7) | (8) | (9) | (10) | (11) | (12) | (13) | (14) |
| Mol. wt. of raw material polyalkyleneimine | Nominal by manufacturer | 1800 | 2000 | 1800 | 1200 | 1200 | 1800 | 10000 | 600 | 1800 | 1200 | 1800 | 1200 | 1300 | 1200 |
| | Wt. av. mol. wt. (GPC, as pullulan) | 5650 | 4850 | 5650 | 4250 | 4250 | 5650 | 15800 | 3000 | 5650 | 4250 | 5650 | 4250 | 3500 | 4250 |
| Wt. av. mol. wt. of polyalkyleneimine derivative (GPC, as polystyrene) | | 4450 | 3850 | 4350 | 3250 | 3200 | 4400 | 14900 | 2300 | 3950 | 2150 | 4400 | 3200 | 2500 | 3200 |
| Substitution ratio (mol %) | | 50 | 70 | 60 | 40 | 60 | 50 | 60 | 40 | 20 | 50 | 50 | 45 | 50 | 40 |
| $R^1$ The number $R^1$ | | 17 | 1, 17 | 17 | 17 | 17 | 17, 19, 21 | 17 | 17 | 17 | 11 | 17 | 17 | 17 | — |
| $R^2$ of carbon $R^2$ | | — | — | — | — | — | — | — | — | — | — | — | 18 | — | 18 |
| $R^3$ atoms $R^3$ | | — | — | — | — | — | — | — | — | — | — | — | — | 18 | — |
| Av. C no. | | 17 | 12.4 | 17 | 17 | 17 | 18.9 | 17 | 17 | 17 | 11 | 17 | 17.2 | 17.4 | 18 |
| C ≥ 13 content (mol %) | | 100 | 71 | 100 | 100 | 100 | 100 | 100 | 100 | 100 | 0 | 100 | 100 | 100 | 100 |
| Linear:branch ratio | | 100:0 | 73:27 | 60:40 | 80:20 | 70:30 | 50:50 | 60:40 | 60:40 | 80:20 | 100:0 | 20:80 | 80:20 | 80:20 | 60:40 |
| (I)/[(I) + (II) + (III)] | | 100 | 100 | 100 | 100 | 100 | 100 | 100 | 100 | 100 | 100 | 100 | 80 | 60 | 0 |
| (II)/[(I) + (II) + (III)] | | 0 | 0 | 0 | 0 | 0 | 0 | 0 | 0 | 0 | 0 | 0 | 20 | 0 | 100 |
| (III)/[(I) + (II) + (III)] | | 0 | 0 | 0 | 0 | 0 | 0 | 0 | 0 | 0 | 0 | 0 | 0 | 40 | 0 |
| Needle penetration extent | | 2 | 45 | 35 | 20 | 30 | 65 | 40 | 50 | 15 | 150 | * | 20 | 20 | 67 |

* Not measurable (needle penetrating without stop into polyalkyleneimine derivative)

Examples 1 to 10, Comparative Examples 1 to 10

Hair cleansing compositions having formulations shown in Table 2 were prepared through a conventional method.

These hair cleansing compositions were assessed in terms of the size of a tress after shampooing and towel drying, rapid drying property, and rise of hair (root). The specific assessment procedures are as follows.

[Measurement of Thickness of Hair Tress after Towel Drying]

Human hair tresses (length: 25 cm, width: 5.5 cm, and weight: 10 g) were bleached, to thereby prepare damaged hair tress samples. Each hair tress sample was lightly rinsed with warm water (40° C.), and excess water was removed therefrom. Subsequently, each hair tress sample was washed with each hair wash composition (0.5 g) for about 30 seconds under sufficient lathering conditions. The thus-treated sample was rinsed for about 30 seconds in a flow of water and then dried with a towel. After towel drying, ten hair tresses were selected at random, and the width (mm) of each hair tress was measured with a rule.

Evaluation of Rapid Drying Property

The aforementioned hair tress samples were hanged inside a thermostat container with a blower (model:

DKN402, Yamato Scientific Co., Ltd.), which was set at 40° C. The weight of each hair tress sample was monitored at predetermined intervals. The time (min) required until the weight of the hair tress sample was returned to the Value before the shampoo treatment with the hair wash composition was measured.

Evaluation of Rise of Hair (Hair Root)

FIG. 1 is a photograph showing the method for evaluating ease of hair rising in the Examples.

Hair filaments were transplanted to a sheet (7 cm×7 cm) at a density of 200 filaments/cm$^2$ and an angle of 60° along the same direction, to thereby prepare a test tress sample (hair filament length: 30 cm). The thus-prepared tress samples were bleached in advance, to reproduce hair damage conditions.

Each tress sample was washed with each hair cleansing composition test sample (2 g) and then rinsed. Subsequently, the tress sample was dried at 50° C. (dryer) under such conditions that the hair tip was oriented downwardly (i.e., the hair was pending). Next, the hair transplantation surface of the tress sample was oriented upwardly, and the entire hair was drawn to the direction opposite the transplant direction. The height from the sheet to the top (top surface) of the hair (height (mm) represented by the arrows in FIG. 1) was measured.

TABLE 2

| | (% by mass) | | Examples 1 | 2 | 3 | 4 | 5 | 6 | 7 | 8 | 9 | 10 |
|---|---|---|---|---|---|---|---|---|---|---|---|---|
| (a) | Polyalkyleneimine derivative | (1) | 0.2 | | | | | | | | | |
| | | (2) | | 0.5 | | | | | | | | |
| | | (3) | | | 0.2 | | | | | | | |
| | | (4) | | | | 0.2 | | | | | | |
| | | (5) | | | | | 0.2 | | | | | |
| | | (6) | | | | | | 0.2 | | | | |
| | | (7) | | | | | | | 0.8 | | | |
| | | (12) | | | | | | | | 0.2 | | |
| | | (13) | | | | | | | | | 0.2 | |
| | | (14) | | | | | | | | | | 0.2 |
| (b) | Ammonium POE(1) lauryl ether sulfate | | 13 | | 10 | 12 | | 8 | | 13 | | 2 |
| | Sodium POE(2) lauryl sulfate | | | 14 | 3 | | 11 | 2 | 15 | | 12 | 12 |
| (c) | Cationized hydroxyethyl cellulose (*1) | | 0.2 | | | 0.3 | 0.2 | | 0.3 | 0.1 | | |
| | Cationized guar gum (*2) | | 0.3 | | 0.5 | | 0.2 | | | | 0.2 | 0.1 |
| | Polyquaternium-52 (*3) | | | 0.4 | | 0.1 | | 0.3 | 0.2 | 0.3 | 0.5 | 0.3 |
| Other | POE(16) lauryl ether | | 3 | 1 | | 1 | 1 | 3 | 1 | 1 | 1 | 0.5 |
| | Monoisodecyl glyceryl ether | | 0.5 | | 0.5 | 0.5 | 0.1 | | 0.2 | 0.5 | | 0.2 |
| | Polyoxypropylene octyl ether | | | 0.5 | 0.5 | | 0.4 | | 0.5 | 0.3 | 0.8 | |
| | Cocamidopropyl betaine | | 1 | 2 | 2 | 2 | 2 | 2 | 2 | 2 | | 2 |
| | High-oleic sunflower oil | | 0.1 | | 0.1 | | | | 0.2 | | | |
| | Lactic acid (90%) | | 0.5 | 0.5 | 0.5 | 0.5 | 0.5 | 0.5 | 0.5 | 0.5 | 0.5 | 0.5 |
| | Sodium chloride | | 0.2 | 0.2 | 0.2 | 0.2 | 0.2 | 0.2 | 0.2 | 0.2 | 0.2 | 0.2 |
| | Potassium hydroxide (pH-adjusting) | | q.s. | q.s. | q.s. | q.s. | q.s. | q.s. | q.s. | q.s. | q.s. | q.s. |
| | Purified water | | bal. | bal. | bal. | bal. | bal. | bal. | bal. | bal. | bal. | bal. |
| pH (20-fold (mass) water dilute, 25° C.) | | | 4.5 | 4.5 | 5.5 | 4.3 | 4.5 | 4.3 | 4.3 | 4.7 | 4.8 | 4.6 |
| Mean particle size (μm) of component (a) (a') | | | 17 | 8 | 17 | 19 | 15 | 22 | 8 | 13 | 2 | 15 |
| Evaluation Hair tress thickness (mm) after towel drying | | | 2 | 2 | 2 | 3 | 2 | 3 | 2 | 2 | 3 | 5 |
| Drying time (min) | | | 6 | 5 | 6 | 6 | 6 | 7 | 5 | 6 | 7 | 9 |
| Rise of hair tress (mm) | | | 35 | 38 | 33 | 32 | 34 | 33 | 34 | 31 | 33 | 30 |

POE = Polyoxyethylene

TABLE 3

| | (% by mass) | | Comparative Examples 1 | 2 | 3 | 4 | 5 | 6 | 7 | 8 | 9 | 10 |
|---|---|---|---|---|---|---|---|---|---|---|---|---|
| (a) | Polyalkyleneimine derivative | (1) | | | | | 0.2 | | | | | |
| | | (4) | | | | | | 0.2 | 0.2 | | | |
| | | (5) | | | | | | | | 0.2 | | |
| (a') | Polyalkyleneimine derivative (not component (a)) | (8) | 0.2 | | | | | | | | | |
| | | (9) | | 0.2 | | | | | | | | |
| | | (10) | | | 0.2 | | | | | | | |
| | | (11) | | | | 0.2 | | | | | | |
| (b) | Ammonium POE(1) lauryl ether sulfate | | 12 | | 11 | 4 | 14 | 15 | | 13 | | |
| | Sodium POE(2) lauryl sulfate | | 2 | 13 | 3 | 10 | | 13 | 12 | | 14 | |
| (c) | Cationized hydroxyethyl cellulose (*1) | | 0.2 | | | 0.4 | | | 0.4 | 0.3 | | |
| | Cationized guar gum (*2) | | | 0.2 | 0.5 | | | 0.4 | | | 0.3 | |
| | Polyquaternium-52 (*3) | | 0.3 | | | | | | | | | 0.4 |
| Other | POE(16) lauryl ether | | 1 | 1 | 1 | 1 | 1 | | 1 | 1 | 1 | 1 |
| | Monoisodecyl glyceryl ether | | 0.5 | 0.2 | 0.3 | 0.5 | 0.1 | | | 0.6 | 0.1 | 0.1 |
| | Polyoxypropylene octyl ether | | | | 0.3 | | 0.1 | | 0.5 | | 0.2 | |
| | Cocamidopropyl betaine | | 2 | 2 | 2 | 2 | 2 | 2 | 2 | 2 | 2 | 2 |
| | High-oleic sunflower oil | | | | | | | | | 4.5 | | |
| | Silicone (*4) | | | | | | | | | | | 2 |

TABLE 3-continued

|  | Comparative Examples | | | | | | | | | |
| (% by mass) | 1 | 2 | 3 | 4 | 5 | 6 | 7 | 8 | 9 | 10 |
| --- | --- | --- | --- | --- | --- | --- | --- | --- | --- | --- |
| Silicone powder |  |  |  |  |  |  |  |  |  | 0.2 |
| Lactic acid (90%) | 0.5 | 0.5 | 0.5 | 0.5 | 0.5 | 0.5 | 0.5 | 0.5 | 0.5 | 0.5 |
| Sodium chloride | 0.2 | 0.2 | 0.2 | 0.2 | 0.2 | 0.2 | 0.2 | 0.2 | 0.2 | 0.2 |
| Potassium hydroxide (pH-adjusting) | q.s. | q.s. | q.s. | q.s. | q.s. | q.s. | q.s. | q.s. | q.s. | q.s. |
| Purified water | bal. | bal. | bal. | bal. | bal. | bal. | bal. | bal. | bal. | bal. |
| pH (20-fold (mass) water dilute, 25•C. | 4.8 | 4.7 | 4.6 | 4.6 | 4 | 4.7 | 4.7 | 4.7 | 4.4 | 4.4 |
| Mean particle size (•m) of component (a) (a') | 20 | 11 | 21 | 16 | 21 | 55 | 0.3 | 19 | — | — |
| Evaluation Hair tress thickness (mm) after towel drying | 11 | 9 | 10 | 9 | 11 | 10 | 9 | 13 | 16 | 10 |
| Drying time (min) | 17 | 14 | 16 | 15 | 16 | 16 | 15 | 19 | 20 | 16 |
| Rise of hair tress (mm) | 22 | 21 | 23 | 25 | 20 | 20 | 23 | 20 | 19 | 23 |

POE = Polyoxyethylene
(*1): Poise C-80M (product of Kao Corporation)
(*2): Jaguar C-17 (product of Rhodia)
(*3): KG-101E-W (product of Kao Corporation)
(*4): Silicone BY29-119 (product of Dow Corning Toray)

Example 11

| | (% by mass) |
| --- | --- |
| Sodium Polyoxyethylene(2) lauryl ether sulfate | 10.6 |
| Sodium lauryl sulfate | 4.0 |
| Cocamidopropyl betaine | 3.0 |
| Polyoxypropylene(3) monooctyl ether | 0.5 |
| Polyalkyleneimine derivative (2) | 0.3 |
| Cationized guar gum (Jaguar C-17, product of Rhodia) | 0.3 |
| Sodium chloride | 0.5 |
| Coconut acid monoethanolamide | 0.4 |
| Lactic acid (90%) | 0.2 |
| Potassium hydroxide | q.s. |
| Perfume | q.s. |
| Purified water | q.s. |

This shampoo provides high releasability of hair filaments of a hair tress after towel drying, realizes favorable rise of hair after drying, and provides excellent volume-increasing effect.

Example 12

| | (% by mass) |
| --- | --- |
| Sodium polyoxyethylene(1) lauryl ether sulfate | 12.0 |
| Lauryl hydroxysulfobetaine liquid (30%) | 3.0 |
| Polyoxyethylene(16) lauryl ether | 2.0 |
| Polyquaternium-52 (KG-101E-W, product of Kao Corporation) | 0.5 |
| Polyalkyleneimine derivative (9) | 0.2 |
| Cationized hydroxyethyl cellulose (Caticelo M-80, product of Kao Corporation) | 0.2 |
| Isodecyl glyceryl ether | 0.5 |
| Malic acid (50%) | 0.1 |
| Ethanol | 0.2 |
| Sodium benzoate | 0.5 |
| *Eucalyptus* extract | 0.05 |
| *Aloe* extract | 0.05 |
| Potassium hydroxide | q.s. |
| Perfume | q.s. |
| Purified water | q.s. |

This shampoo provides high releasability of hair filaments of a hair tress after towel drying, realizes favorable rise of hair after drying, and provides excellent volume-increasing effect.

Example 13

| | (% by mass) |
| --- | --- |
| Ammonium polyoxyethylene(1) lauryl ether sulfate | 11.0 |
| Isodecyl glyceryl ether | 0.8 |
| Lauryl hydroxysulfobetaine liquid (30%) | 5.0 |
| Polyethyleneimine derivative (2) | 0.2 |
| Cationized guar gum (Jaguar C-14S, product of Rhodia) | 0.4 |
| Dimethyldiallylammonium chloride-acrylamide copolymer liquid (Merquat 550, product of The Lubrizol Corporation) | 1.0 |
| Lauric acid (Lunac L-98, product of Kao) | 0.5 |
| Ethylene glycol distearyl | 1.7 |
| Benzyl alcohol | 0.3 |
| Malic acid (50%) | 0.75 |
| Dipropylene glycol | 1.0 |
| Dimethylpolysiloxane | 0.5 |
| Orange oil | 0.05 |
| Menthol | 1.0 |
| Potassium hydroxide | q.s. |
| Perfume | q.s. |
| Purified water | q.s. |

This shampoo provides high releasability of hair filaments of a hair tress after towel drying, realizes favorable rise of hair after drying, and provides excellent volume-increasing effect.

Example 14

| | (% by mass) |
| --- | --- |
| Sodium polyoxyethylene(1) lauryl ether sulfate | 12.0 |
| Isodecyl glyceryl ether | 0.4 |
| Lauryl hydroxysulfobetaine liquid (30%) | 4.0 |
| Myristyl alcohol | 0.3 |

-continued

|  | (% by mass) |
|---|---|
| Polyquaternium-52 (KG-101E-W, product of Kao Corporation) | 0.5 |
| Polyalkyleneimine derivative (9) | 0.2 |
| Cationized guar gum (Jaguar C-17, product of Rhodia) | 0.3 |
| Dimethyldiallylammonium chloride-acrylamide copolymer liquid (Merquat 550, product of The Lubrizol Corporation) | 0.2 |
| Polyoxypropylene(3) monooctyl ether | 0.5 |
| Ethylene glycol distearyl | 2.0 |
| Benzyl alcohol | 0.3 |
| Malic acid (50%) | 0.75 |
| Dipropylene glycol | 1.0 |
| Amino-modified polysiloxane | 0.3 |
| Sunflower oil | 0.05 |
| Sodium chloride | 1.0 |
| Potassium hydroxide | q.s. |
| Perfume | q.s. |
| Purified water | q.s. |

This shampoo provides high releasability of hair filaments of a hair tress after towel drying, realizes favorable rise of hair after drying, and provides excellent volume-increasing effect.

The invention claimed is:

1. A hair cleansing composition which comprises the following components (a), (b), and (c), component (a) being in the form of particles having a mean particle size of from 0,5 μm to 50 μm, wherein the components (a), (b), and (c) are:
   (a) a polyalkyleneimine derivative or a salt thereof, the derivative formed of a polyalkyleneimine having a weight average molecular weight of from 3,300 to 50,000, in which at least one of the substituents represented by any of formulas (I), (II), and (III) is bonded to 40 mol% or more of the nitrogen atoms of the polyalkyleneimine, the formulas being:

$$R^1\text{—CO—} \tag{I}$$

$$R^2\text{—}(CH_2)_n\text{—CHX—}CH_2\text{—} \tag{II}$$

$$R^3\text{—NH—CO—} \tag{III}$$

wherein, in formula (I), $R^1$ represents a group selected from the group consisting of a hydrogen atom, and an alkyl group, an alkeny group, and a hydroxyalkyl group, in the form of a linear-chain group or a branched-chain group;
   in formula (II), $R^2$ represents a group selected, from among a hydrogen atom, and an alkyl group, an alkoxy group, an alkenyl group, and an alkenyloxy group, in the form of a linear-chain group or a branched-chain group; n is an integer of 0 or 1; when $R^2$ is a hydrogen atom, a linear-chain or a branched-chain alkyl group, or a linear-chain or a branched-chain alkenyl group, n is 0; when $R^2$ is an alkoxy group or an alkenyloxy group, n is 1; and X represents a hydrogen atom or a hydroxyl group;
   in formula (III), $R^3$ represents a group selected from the group consisting of a hydrogen atom, and an alkyl group and an alkenyl group, in the form of a linear-chain group or a branched-chain group; and
   $R^1$, and $R^2$, and $R^3$ may be identical to or different from one another, and at least one of $R^1$, $R^2$, and $R^3$ is a group having 13 or more carbon atoms; the entirety of $R^1$, $R^2$, and $R^3$ has an average number of carbon atoms of 9 or more; and the of $R^1$, $R^2$, $R_3$ has a linear group content of 30 mol% or more;
   (b) an anionic surfactant; and
   (c) a water-soluble cationic polymer.

2. The hair cleansing composition according to claim 1, wherein in component (a), the entirety of $R^1$, $R^2$, and $R^3$ has a linear group content of from 40 mol% or more to 90 mol% or less.

3. The hair cleansing composition according to claim 1, wherein, in component (a), the ratio of the number of groups represented by formula (I) to the number of all substituents is 20 mol% or more, and the ratio of the total number of groups represented by formulas (II) and (III) to the number of all substituents is 80 mol% or less.

4. The hair cleansing composition according to claim 1, which has an extent of needle penetration of component (a), as measured at 25°C according to ASTM D1321, of from 2 or more to 100 or less.

5. The hair cleansing composition according to claim 1, wherein the component (a) content is 0.05 by mass or more to 10.0 by mass or less.

6. The hair cleansing composition according to claim 1, wherein the component (a) content is 0.1 by mass or more to 3.0 by mass or less.

7. The hair cleansing composition according to claim 1, wherein the anionic surfactant of component (b) is selected, from the group consisting of a sulfuric acid-type surfactant, a silfonic acid-type surfactant, and a carboxylic acid-type surfactant.

8. The hair cleansing composition according to claim 1, wherein the anionic surfactant of component (b) ts selected from the group consisting of an alkylsulfate salt., a polyoxyalkylene alkyl ether sulfate salt, a polyoxyalkylene alkenyl ether sulfate salt, a sulfosuccinic acid alkyl ester salt, a sultbsuccinic acid alkylene alkyl phenyl ether sulfate salt, an alkanesulfonate salt, a higher fatty acid salt, and an alkyl ether carboxylic acid or a salt thereof.

9. The hair cleansing composition according to claim 1, wherein the anionic. surfactant of component (b) is a surfactant represented by the following formula (IV) or (V):

$$RO(CH_2CH_2O)_nSO_3M \tag{IV}$$

$$ROSO_3M \tag{V}$$

wherein R represents a C10 to C18 alkyl group or alkenyl group; M represents an alkali metal, an alkaline earth metal, or an ammonium; n is a weight-average number of from 1 to 5.

10. The hair cleansing composition according to claim 1, wherein the component (b) content is 1 % by mass or more to 30% by mass or less.

11. The hair cleansing composition according to claim 1, wherein the component (b) content is 5% by mass or more to 25% by mass or less.

12. The hair cleansing composition according to claim 1, wherein the component (b) content is 8% by mass or more to 20% by or less.

13. The hair cleansing composition according to claim 1, wherein the water-soluble cationic polymer of component (c) is selected from the group consisting of a canonized cellulose derivative, a canonized guar gum derivative, a diallyl quaternary ammonium salt-acrylamide copolymer, and an N,N-dimethylaminoethyl methacrylate diethylsulfate-N,N-dimethvlacrylamide-polyethylene glycol dimethacrylate copolymer.

14. The hair cleansing composition according to claim 1, wherein the component (c) content is 0.01% by mass or more to 5% by mass or less.

15. The hair cleansing composition according to claim 1, wherein the component (c) content is 0.1% by mass or more to 2% by mass or less.

16. The hair cleansing composition according to claim 1, wherein the hair cleansing composition comprises a total amount of a non-volatile solvent and oily agent which are liquid at ambient temperature and have a solubility parameter δ of 20 or less of 4.0% by mass or less, or wherein the hair cleansing composition is free from the non-volatile solvent and oily agent.

17. The hair cleansing composition according to claim 1, which contains at least water as a medium.

18. A method for increasing the volume of hair, comprising applying to hair the hair cleansing composition according to claim 1, spreading the hair cleansing composition over the hair, and rinsing off the hair cleansing composition.

* * * * *